United States Patent [19]

Mannheimer

[11] Patent Number: 5,746,206
[45] Date of Patent: *May 5, 1998

[54] ISOLATED LAYER PULSE OXIMETRY

[75] Inventor: Paul D. Mannheimer, Belmont, Calif.

[73] Assignee: Nellcor Incorporated, Pleasanton, Calif.

[*] Notice: The term of this patent shall not extend beyond the expiration date of Pat. No. 5,524,617

[21] Appl. No.: 662,439

[22] Filed: Jun. 10, 1996

Related U.S. Application Data

[63] Continuation of Ser. No. 403,642, Mar. 14, 1995, Pat. No. 5,524,617.

[51] Int. Cl.$^6$ ............................................. A61B 5/00
[52] U.S. Cl. ............................................. 125/633; 356/39
[58] Field of Search ................................. 128/633, 664, 128/665; 356/41

[56] References Cited

U.S. PATENT DOCUMENTS

| | | | |
|---|---|---|---|
| 4,700,708 | 10/1987 | New, Jr. et al. | 128/633 |
| 4,796,636 | 1/1989 | Branstetter et al. | 128/633 |
| 5,057,695 | 10/1991 | Hirao et al. | 128/633 |
| 5,139,025 | 8/1992 | Lewis et al. | 128/665 |
| 5,188,108 | 2/1993 | Secker | 128/633 |
| 5,218,962 | 6/1993 | Mannheimer et al. | 128/633 |
| 5,226,417 | 7/1993 | Swedlow et al. | 128/633 |
| 5,277,181 | 1/1994 | Mendelson et al. | 128/633 |
| 5,285,783 | 2/1994 | Secker | 128/633 |
| 5,297,548 | 3/1994 | Pologe | 128/633 |
| 5,372,135 | 12/1994 | Mendelson et al. | 128/633 |
| 5,524,617 | 6/1996 | Mannheimer | 128/633 |

FOREIGN PATENT DOCUMENTS

| | | |
|---|---|---|
| 4304693 A1 | 8/1994 | Germany . |
| WO 92/21283 | 12/1992 | WIPO . |

*Primary Examiner*—Jennifer Bahr
*Assistant Examiner*—Eric F. Winakur
*Attorney, Agent, or Firm*—Nawrocki, Rooney & Sivertson

[57] ABSTRACT

An apparatus of and method for measuring arterial blood oxygen saturation at a particular tissue level of interest. Visible and near infrared radiation is emitted into a patient at the measurement site using two different wavelengths. Detection at two different detection sites permits rejection of oxygen saturation at undesired tissue levels.

6 Claims, 8 Drawing Sheets

ISOLATED LAYER PULSE OXIMETRY

This is a continuation application of U.S. application Ser. No. 08/403,642, filed Mar 14, 1995 now U.S. Pat. No. 5,524,617.

BACKGROUND OF THE INVENTION

1. Field of the Invention

The present invention generally relates to instruments which operate on the principal of pulse oximetry and more particularly relates to instruments which non-invasively measure oxygen saturation of arterial blood in vivo.

2. Description of the Prior Art

Light in the visible and near infrared region of the electromagnetic spectrum has been used for the in vivo measurement of oxygen saturation levels of a patient's blood. Lewis et al. in U.S. Pat. No. 5,139,025 and Lewis et al. in International Publication (PCT) Number WO 92/21283 discuss spectrophotometric instruments whereby the oxygen saturation of blood, both venous and arterial combined, is estimated using at least three electromagnetic sensor areas. A disadvantage of such instruments is that the accuracy of the oxygen saturation calculation is limited due to such calculation's sensitivity to varying parameters of the tissue other than blood saturation, for example a change in concentration. Rall, et al. in German Patent No. DE 43 04 693 teaches the use of a plurality of light sensors with a single light detector as the best means for oximetry measurement in the particular shape of the device of the invention, primarily intended for connection to a fetus.

New, Jr. et al. in U.S. Pat. No. 4,700,708, the disclosure of which is incorporated by reference, calculates arterial oxygen saturation by isolating the change in detected light intensities during a cardiac cycle in an attempt to minimize and even eliminate the light scattering and absorption effects of non-arterial blood tissue of a patient. Though this technique, known as pulse oximetry, is effective in eliminating many of the artifacts introduced by bone, skin, muscle, etc. a disadvantage exists in that the signal acquisition and computation circuits must be very robust since the useful part of the signal is the relatively small change in detected intensities, as opposed to the total detected intensity. Another disadvantage is that the calculated oxygen saturation value is influenced by pulsatile signal contributions from many differing tissue layers, including the skin or surface tissue layer. It is often desirable to know the arterial oxygen saturation of a particular tissue layer or range of tissue layers as opposed to knowing only a general average arterial oxygen saturation value for all layers, because the oxygen saturation value of the multiple layers may differ from one another. Some clinical conditions, such as stasis, may continue to provide a pulsatile signal in the absence of flow, particularly near the outer surface.

U.S. Pat. No. 5,188,108 issued to Secker, suggests the use of a plurality of emitters and/or receivers to provide multiple emitter/receiver combination. The emitter/receiver spacing for each combination is selected to provide equivalent optical path lengths between combinations using different wavelengths of emission.

SUMMARY OF THE INVENTION

The present invention overcomes the disadvantages found in the prior art by providing a pulse oximetry system for the determination of arterial blood oxygen saturation level at a particular depth of tissue which readily compensates for limitations induced in the prior art systems. Specifically, the present invention allows for pulsed oximetry measurement which isolates arterial saturation levels for particular ranges of tissue layers which rejects saturation levels of the tissue above or below the tissue of interest by utilizing multiple spaced detectors and/or emitters.

According to one embodiment of the invention, a sensor for use with a pulse oximeter monitor comprises a patient interface housing for coupling to a patient; at least three sensor areas for emitting electromagnetic radiation which penetrates tissue of the patient and detects that electromagnetic radiation scattered by the tissue, a spacing between a first pair of electromagnetic emitter and electromagnetic detector being different than that of a spacing between a second pair of electromagnetic emitter and electromagnetic detector; and means for calculating an arterial oxygen saturation level of the patient in response to the detected electromagnetic radiation.

According to two preferred embodiments, the sensor areas comprise first and second separated and spaced apart emitter areas each capable of generating light of at least two distinct wavelengths, and a detector, the first emitter area and the detector corresponding to a first pair of emitter and detector, the second emitter area and the detector corresponding to the second pair of emitter and detector; or the sensor areas comprise first and second detector areas each capable of detecting light of at least two separate wavelength values, and an emitter area capable of generating said light having the at least two separated wavelength values.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1A:
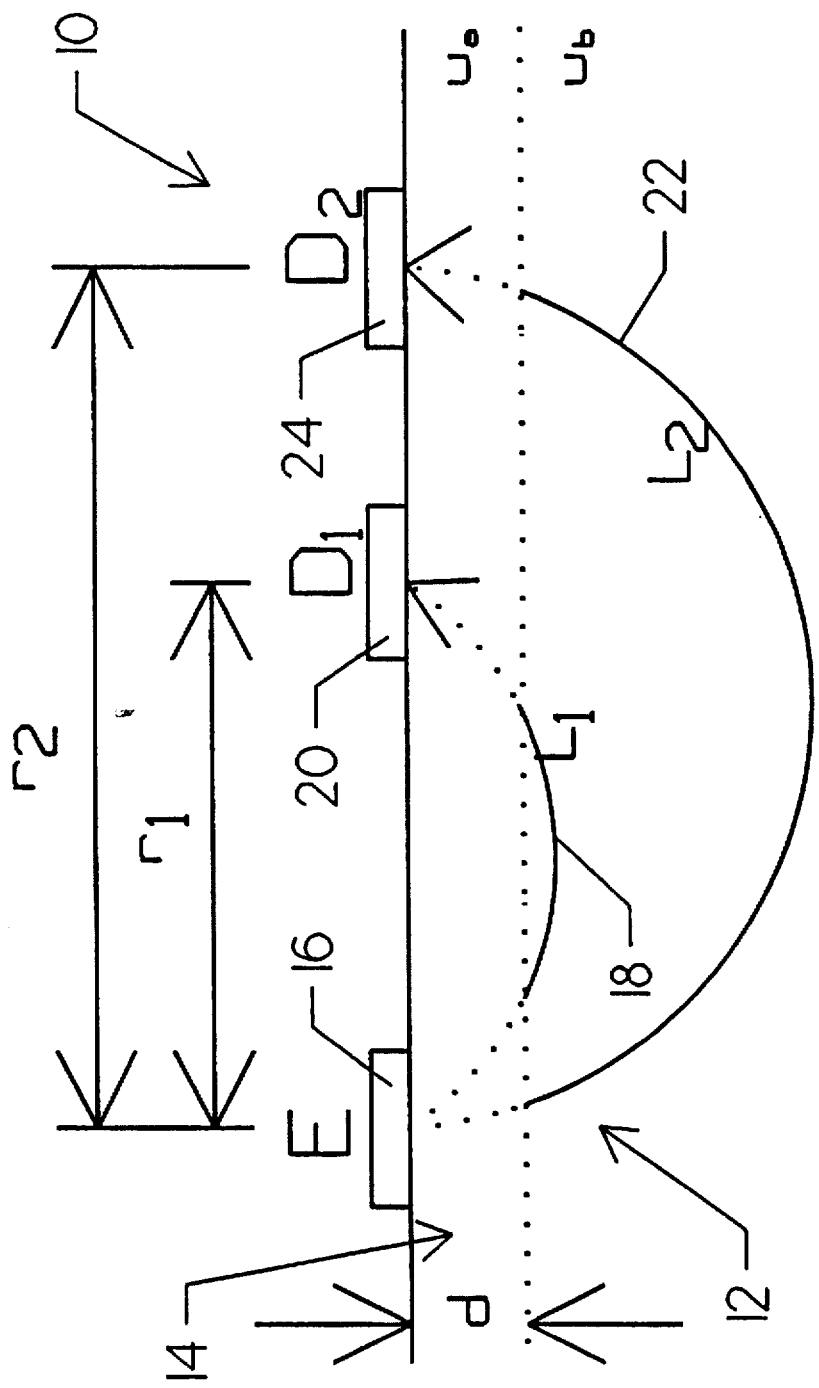
FIG. 1A is a schematic diagram showing the basic principles of the present invention using a single emitter and multiple detectors.

FIG. 1A is a schematic diagram showing the principles of operation of the present invention. In this example, it is assumed desirable to measure the percentage of oxygen saturation within the arterial blood of patient 10 at subdermal tissue level 12 having light absorption properties $u_b$. Interposed between the non-invasive monitoring and measurement system (not shown) and subdermal tissue level 12, is skin or surface tissue level 14 having light absorption properties $u_a$. It is deemed desirable to measure arterial oxygen saturation in the tissue layer 12 or the tissue layer 14 independently.

According to a first preferred embodiment, emitter 16 transmits electromagnetic radiation in the visible and near infrared region at two predetermined wavelengths (e.g. 660 nm and 905 nm). Emitter 16 is shown as a single entity in this example. However, different emitters may be used for the different predetermined wavelengths, if desired. If more than one emitter is used, it is most convenient that they be co-located to simulate a single point source. LED's are a preferred type of emitter. The signals from emitter 16 travel generally along path 18 to a first detector 20 and along path 22 to a second detector 24 as shown. The length of path 18 within layer 12 (with absorption $u_b$) is shown as $L_1$ and the length of path 22 within layer 12 is shown as $L_2$.

Detector 20 is spaced a distance of $r_1$ from emitter 16 and detector 24 is spaced at a distance of $r_2$.

As can be seen in the drawing, both path 18 and path 22 traverse skin layer 14 twice. Furthermore, because paths 18 and 22 traverse skin layer 14 using approximately the same angle, the primary difference between paths 22 and 18 is the difference between length $L_2$ and length $L_1$ traversing subdermal layer 12, which is the tissue layer of interest. Therefore, it can be assumed that the difference in absorption between path $L_2$ and path $L_1$ is directly attributable to subdermal layer 12, the tissue layer of interest, corresponding to the different spacings $r_2$ and $r_1$.

The path length through skin layer 12 may be represented by l and the deeper path through the subdermal tissue by $L_1$ and $L_2$, depending on which detector is considered. Note that multiple emitters may transmit to a single detector as discussed below in relation to FIG. 1B. Following the formalism of Beer's Law, the signal detected at $D_1$ 20 is given by:

$$I_1 = I_o \exp(-u_a l) \cdot \exp(-u_b L_1) \cdot \exp(-u_a l) \quad (1)$$

which describes the attenuation of the signal traveling twice through the skin layer 14 and once through the subdermal tissue 12 where:

$I_1$ = the detected light intensity at $D_1$
$I_o$ = the emitted light intensity of emitter E
$u_a$ = the characteristic absorption of layer 14
$u_b$ = the characteristic absorption of layer 12
l = the path length through layer 14
$L_1$ = the path length through layer 12

The absorption coefficients can be rewritten as the product of the concentration of an absorbing constituent, [c], and its extinction coefficient $\beta$. In this case, [c] is the concentration of total hemoglobin in the tissue. Allowing for different concentrations in the two layers, equation 1 becomes:

$$I_1 = I_o \exp(-2\beta_a[c_a]l - \beta_b[c_b]L_1) \quad (2)$$

To include the venous contribution, $\beta$[c] expands as follows:

$$\beta[c] \text{ becomes } \beta_{art}[c]_{art} + \beta_{ven}[c]_{ven} \quad (3)$$

Next is added the feature of pulse oximetry. Consider that the arterial blood concentration in both upper and lower layers vary with time following the cardiac cycle, and that the two layers may additionally have different pulse amplitudes. Assume the background venous blood concentration does not vary with the cardiac cycle. Taken at any convenient point in time (e.g. maxima or minima of the cardiac cycle), the logarithm of equation 2, considering equation 3, becomes:

$$\ln(I_1(t_1)) = I_o - 2(\beta_{a,art}[c_a(t_1)]_{art} + \beta_{a,ven}[c_a]_{ven})l - (\beta_{b,art}[c_b(t_1)]_{art} + \beta_{b,ven}[c_b]_{ven})L_1 \quad (4)$$

Subtracting the signal observed at a second point in time, this expression simplifies:

$$\ln(I_1(t_1)) - \ln(I_1(t_2)) = -2(\beta_{a,art}\Delta[c_a]_{art})l - (\beta_{b,art}\Delta[c_b]_{art})L_1 \quad (5)$$

where $\Delta[c]_{art} = [c(t_1)]_{art} - [c(t_2)]_{art}$. Recalling that we assume the contribution of the skin layer has the same influence on both detectors, we can write a similar expression for the signals observed at detector $D_2$:

$$\ln(I_2(t_1)) - \ln(I_2(t_2)) = -2(\beta_{a,art}\Delta[c_a]_{art})l - (\beta_{b,art}\Delta[c_b]_{art})L_2 \quad (6)$$

Subtracting equation 6 from equation 5, we find:

$$[\ln(I_1(t_1)) - \ln(I_1(t_2))] - [\ln(I_2(t_1)) - \ln(I_2(t_2))] = \beta_{b,art}\Delta[c_b]_{art}(L_2 - L_1) \quad (7)$$

Notice that the contribution of the skin layer has been eliminated. Finally, the measurements are repeated at a second wavelength. Taking the ratio of equation 7 evaluated at two wavelengths gives:

$$R = ([\ln(I_1(t_1)) - \ln(I_1(t_2))] - [\ln(I_2(t_1)) - \ln(I_2(t_2))])_{\lambda 1} / ([\ln(I_1(t_1)) - \ln(I_1(t_2))] - [\ln(I_2(t_1)) - \ln(I_2(t_2))])_{\lambda 2} = \beta_{b,art,\lambda 1}(L_2 - L_1)_{\lambda 1} / \beta_{b,art,\lambda 2}(L_2 - L_1)_{\lambda 2} \quad (8)$$

Equation 8 is equivalent to conventional pulse oximetry if the second detector is eliminated. In the conventional, nonscattering, model of oximetry, it is assumed that the average path lengths are equal at the two wavelengths—and they would simply drop out of equation 8. The model is improved, however, if the ratio of the average path lengths, or in this case the ratio of the difference lengths, is kept as an empirically determined correction factor:

$$R = \beta_{b,art,\lambda 1}/\beta_{b,art,\lambda 2} \cdot \Delta L_{\lambda 1}/\Delta L_{\lambda 2} \quad (9)$$

where $\Delta L = L_2 - L_1$. In conventional pulse oximetry, the ratio of average path lengths is stable over a useful (but limited) saturation range. With the proper choice of wavelengths, this useful range can be engineered to cover specific meaningful clinical windows (e.g., 70–100% saturation or 40–60% saturation).

The extinction coefficient can be rewritten in oxygen saturation terminology as:

$$\beta = S \cdot \beta_{oxy} + (1-S) \cdot \beta_{red} \quad (10)$$

Where $S = [O_2Hb]/([O_2Hb] + [Hb])$ and where $\beta_{oxy}$ refers to oxygenated hemoglobin ($O_2Hb$) and $\beta_{red}$ refers to reduced hemoglobin (Hb)

From this point on in the derivation, everything follows the conventional approach to pulse oximetry, applying equation 10 to 9, and solving for $S(S_p,O_2)$ in terms of the observation R:

$$S_pO_2 = [\beta_{red,\lambda 2} - R \cdot \beta_{red,\lambda 1}] / [R \cdot (\beta_{oxy,\lambda 1} - \beta_{red,\lambda 1}) - \beta_{oxy,\lambda 2} + \beta_{red,\lambda 2}] \quad (11)$$

In equation 11, the ratio of $\Delta L$'s has been absorbed into the appropriate $\beta$'s as these will ultimately be determined empirically according to a preferred embodiment of the invention.

This result differs from the conventional single detector pulse oximetry algorithm in that the skin layer signals are excluded from the measurement, regardless if the skin pulses or is non-pulsatile (e.g., vasoconstriction or exsanguination). Within the limitations of the assumptions made, as long as the upper skin layer does not create a shunt, and the deeper layer continues to pulse, this algorithm gives a result related only to the arterial blood saturation of the deeper tissue.

The separation of the first emitter/detector pair 16,20 (i.e. $r_1$) and the second emitter/detector pair 16,24 (i.e. $r_2$) should be larger than several times the skin thickness (i.e. $r_1, r_2$ much greater than d) so that the four occurrences of are all approximately equal, or at least have equivalent counterparts influencing the two detectors. The detector separation from the emitter should also be large enough to probe "deep" enough, the probed depth somewhat less than the separation. The two detectors should not be too far separated from one another, however, or else the assumption of equivalent skin thickness may be violated. If the detectors are too close to each other, $\Delta L$ becomes 0 and the measurement becomes unstable (see equation 9).

It is also possible to solve for the skin's saturation explicitly, excluding the contribution of deeper pulsating tissues. Instead of subtracting equation 6 from 5, multiply equation 5 by $L_2$ and equation 6 by $L_1$, then subtract to form:

$$L_2 \cdot [\ln(I_1(t_1)) - \ln(I_1(t_2))] - L_1 \cdot [\ln(I_2(t_1)) - \ln(I_2(t_2))] = 2(L_1 - L_2)|\beta_{a,art} \Delta [c_a]_{art} \quad (12)$$

The quotient of equation 12, evaluated at the two wavelengths becomes:

$$(L_2 \cdot \ln[I_1(t_1)/I_1(t_2)] - L_1 \cdot \ln[I_2(t_1)/I_2(t_2)])_{\lambda 1}/(L_2 \cdot \ln[I_1(t_1)/I_1(t_2)] - L_1 \cdot \ln[I_2(t_1)/I_2(t_2)])_{\lambda 2} = [(l \Delta L)_{\lambda 1}/(l \Delta L)_{\lambda 2} \cdot (\beta_{a,art,\lambda 1}/\beta_{a,art,\lambda 2})] \quad (13)$$

Now, utilizing the concept of the path length multiplier, defined as L/r, M will refer to the subdermal tissue and m for the skin layer. If $\Delta L$ is much less than $r_1$, one can approximate that the path length multipliers are the same for the two detectors. This leaves us with:

$$M_{\lambda 1} = L_{1,\lambda 1}/r_1 \text{ approximates } L_{2,\lambda 1}/r_2; \; m_{\lambda 1} = l_{\lambda 1}/d \quad (14a)$$

$$M_{\lambda 2} = L_{1,\lambda 2}/r_1 \text{ approximates } L_{2,\lambda 2}/r_2; \; m_{\lambda 2} = l_{\lambda 2}/d \quad (14b)$$

Substituting these definitions into equation 13 simplifies the result into a more useful form:

$$R = (r_2 \cdot \ln[I_1(t_1)/I_1(t_2)] - r_1 \cdot \ln[I_2(t_1)/I_2(t_2)])_{\lambda 1}/(r_2 \cdot \ln[I_1(t_1)/I_1(t_2)] - r_1 \cdot \ln[I_2(t_1)/I_2(t_2)])_{\lambda 2} = m_{\lambda 1}/m_{\lambda 2} \cdot \beta_{a,art,\lambda 1}/\beta_{a,art,\lambda 2} \quad (15)$$

As with the subdermal calculation, the ratio of $m_{\lambda 1}/m_{\lambda 2}$ can be absorbed into the empirically determined constants. And just as in the previous calculation, the path-length-multiplier ratio is adequately stable over limited, but useful, windows of saturation. The positioning of the two detectors takes on more importance here, and thus would need to be reproducible in a preferred sensor embodiment. Calculation of $S_pO_2$ follows in the same manner as in equations 9 through 11.

Figure 1B:
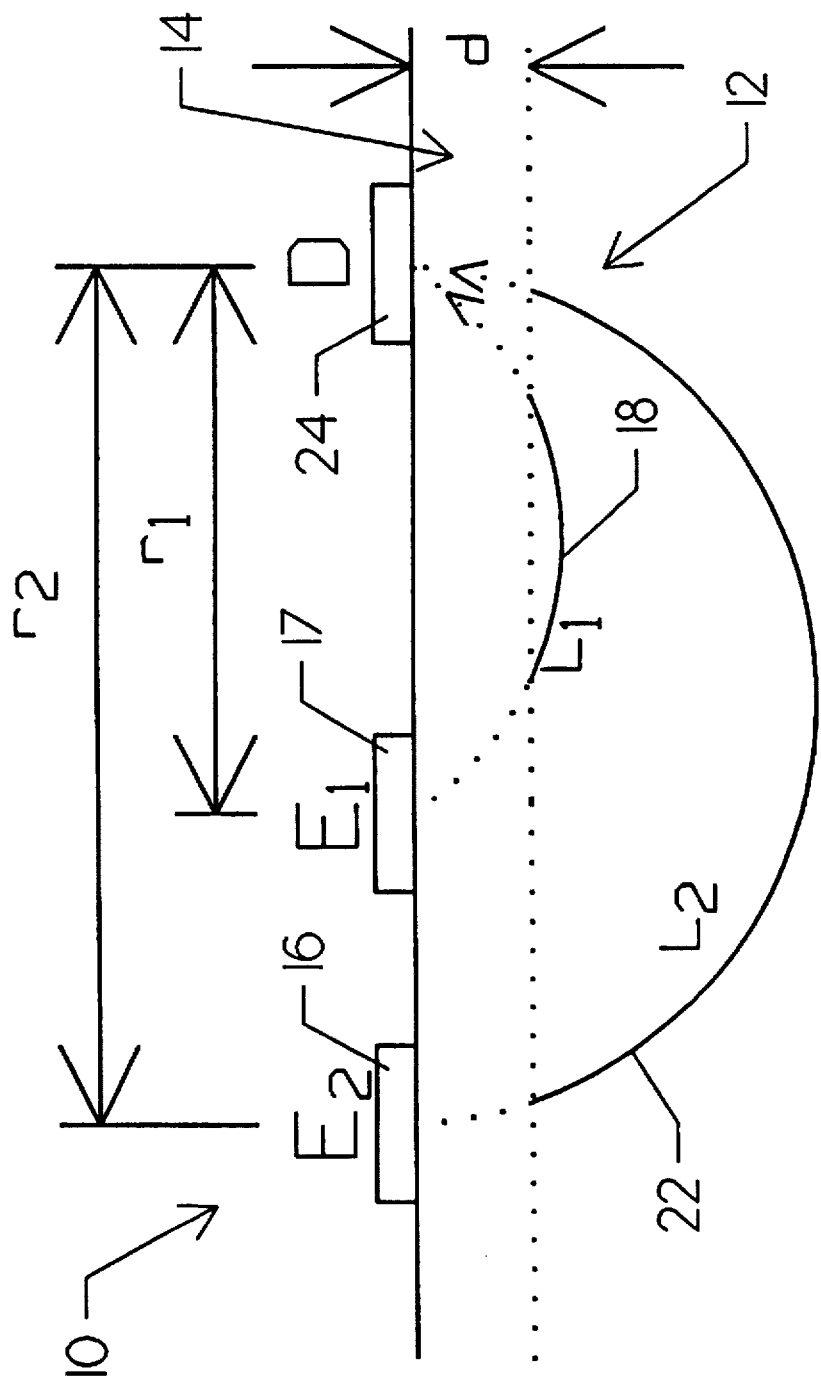
FIG. 1B shows an alternative approach using multiple emitters and a single detector.

FIG. 1B is a schematic diagram, similar to FIG. 1A, showing the present invention employing multiple emitters 16 and 17 and a single detector 24. Those of skill in the art will appreciate that the operation is similar to that described above.

Figure 2:
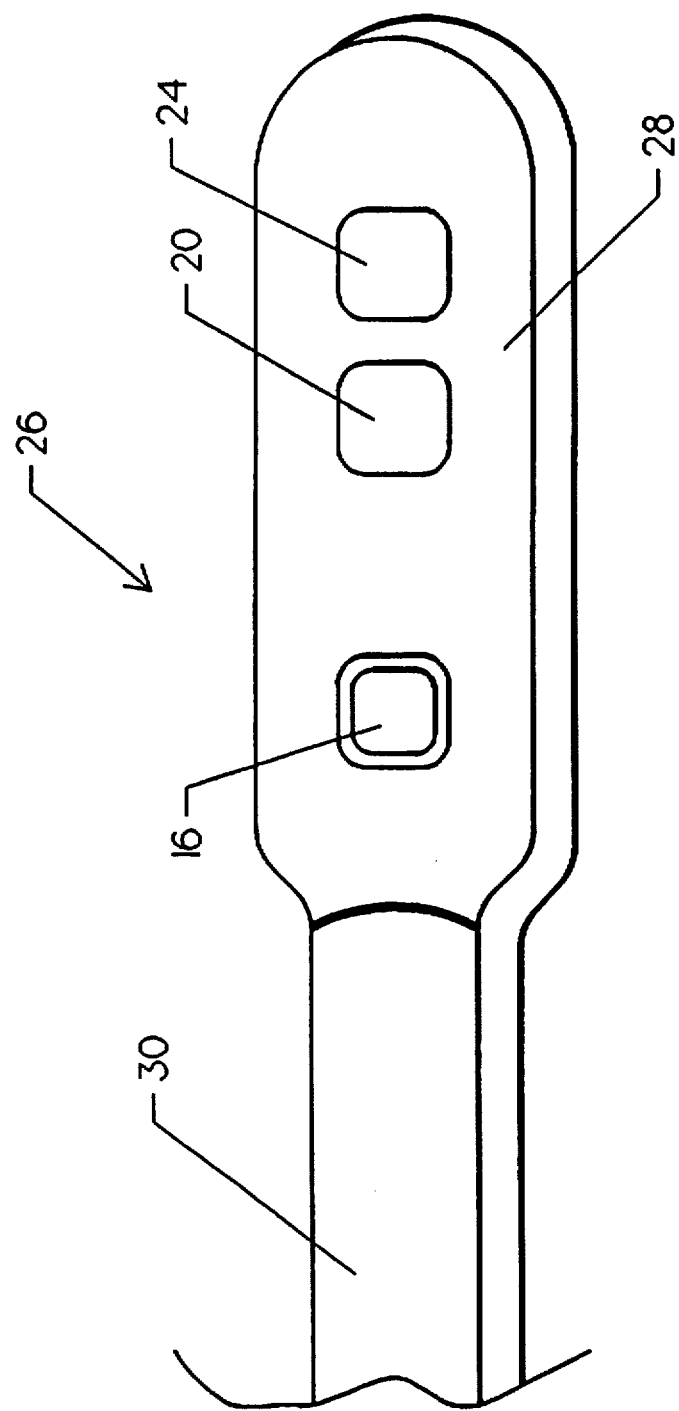
FIG. 2 is a closeup perspective view of a portion of the patient contact element.

FIG. 2 is a perspective view of the preferred mode of patient interface device 26 employing the present invention. Planar surface 28 is placed into contact with the skin of the patient during monitoring and measurement. If desirable, this position may be maintained via adhesive or other mechanical means known in the art. Further, if desirable, surface 28 may have a curvature, and may be either flexible or rigid.

During the time that planar surface 28 is in position, emitter 16, detector 20, and detector 24 are in direct contact with the skin of the patient (see also FIG. 1). The spacing of emitter 16, detector 20, and detector 24 are as previously discussed.

Wiring, not shown in this view, electrically couples emitter 16, detector 20, and detector 24 to the circuitry which performs the monitoring functions.

Figure 3:
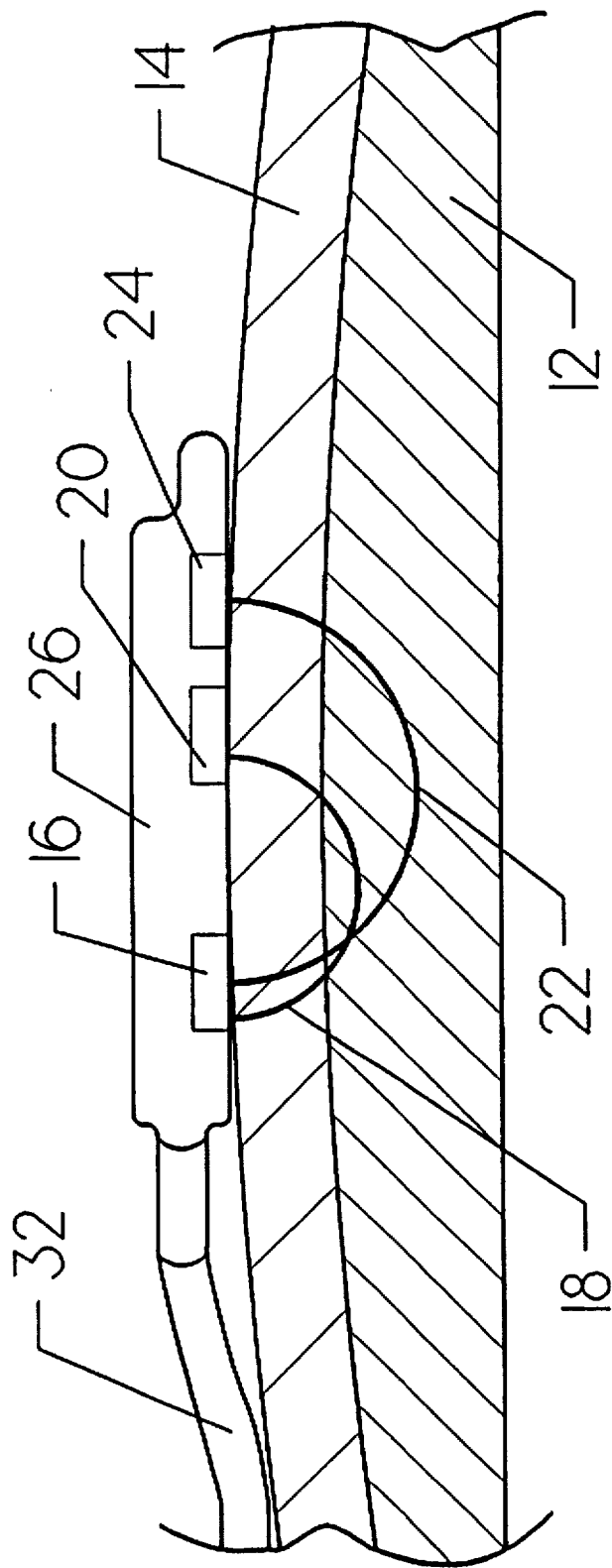
FIG. 3 is a partially sectioned view showing the operation of the present invention in vivo.

FIG. 3 is a partially sectioned view showing patient interface device 26 in operational position. Cable 32 conducts the electrical signals to and from the monitoring circuitry as described below. All other elements are as previously described.

Figure 4:
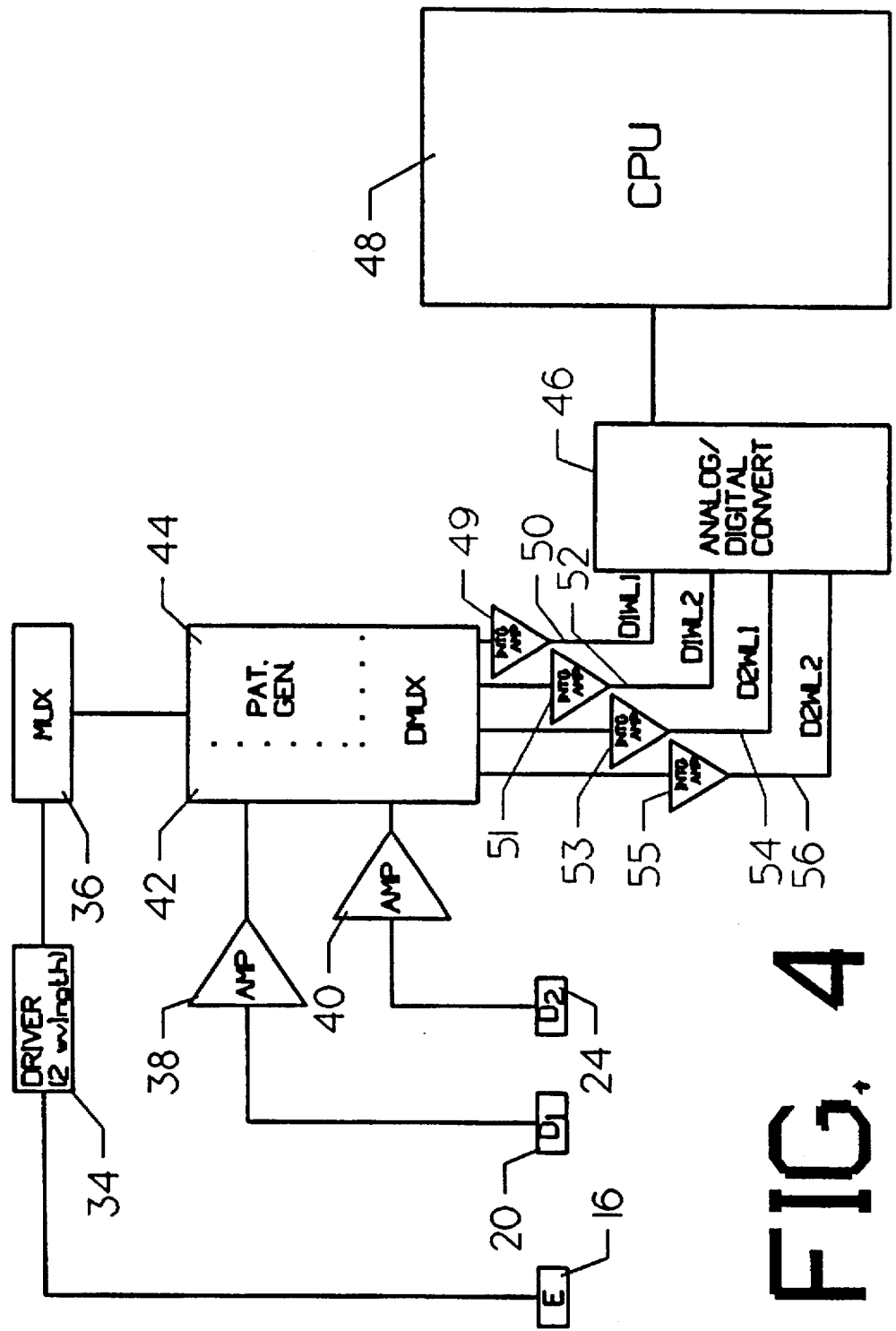
FIG. 4 is an overall block diagram showing the major components of an operational system employing the present invention.

FIG. 4 is a block diagram showing the entire monitoring and measurement system employing the present invention. According to a first preferred embodiment, multiplexer 36 and two wavelength driver 34 alternately turn on the red and infrared LED's 16 at a desired chop frequency (e.g. 1,600 hz). These red and infrared signals are detected by detectors 20 and 24 and amplified by current-to-voltage amplifiers 38 and 40. The outputs of transconductance amplifiers 38 and 40 are demultiplexed by DMUX 42 so as to generate a first and second wavelength signal for each of detectors $D_1$ (20) and $D_2$ (24), which generated signals are sent through integrating amplifiers 49, 51, 53 and 55 to be placed on, respectively, lines 50, 52, 54 and 56. These first and second wavelength signals are digitized by Analog/Digital Converter 46. The digitized signals are transmitted to CPU 48 for calculating arterial oxygen saturation. A preferred architectural implementation of the control electronics is disclosed in PCT/US94/03546, the disclosure of which is incorporated herein by reference. Alternate control electronics are known in the art and could be used, if desired.

As previously described, if deep tissue properties are desired, CPU 48 calculates R using equation 8 and $S_pO_2$ using equation 11 with constants $\beta_{red,\lambda 2}, \beta_{red,\lambda 1}, \beta_{oxy,\lambda 1}$, and $\beta_{oxy,\lambda 2}$ being stored in CPU memory, having been previously determined empirically. If shallow tissue properties are desired, CPU 48 calculates R using equation 15 and $S_pO_2$ using equation 11.

According to a preferred embodiment, CPU 48 identifies and qualifies arterial pulses from the signals $D_1, \lambda_1; D_1, \lambda_2; D_2, \lambda_1, D_2, \lambda_2$ using any of the signal processing techniques described in U.S. Pat. Nos. 4,869,254; 5,078,136; 4,911,167; 4,934,372; 4,802,486; and 4,928,692, the disclosures of which are all incorporated herein by reference.

In addition, though R is determined in equations (8), (15) using maximum and minimum intensities occurring during the cardiac cycle, other points in the cardiac cycle could be utilized as well, including adjacent digital points using derivative signal processing techniques described in PCT/US94/03546 cited above.

According to a preferred embodiment, one wavelength is chosen from the red portion of the electromagnetic spectrum (e.g. 660 nm) and the other wavelength is chosen from the near infrared portion of the electromagnetic spectrum (e.g. 900 nm). The precise wavelength values are a matter of design choice depending on the application. For sensors for detecting fetal arterial oxygen saturation, a preferred wavelength pair is 735 nm, 905 nm, as disclosed in U.S. patent application Ser. No. 08/221,911, the disclosure of which is incorporated herein by reference.

Figure 5:
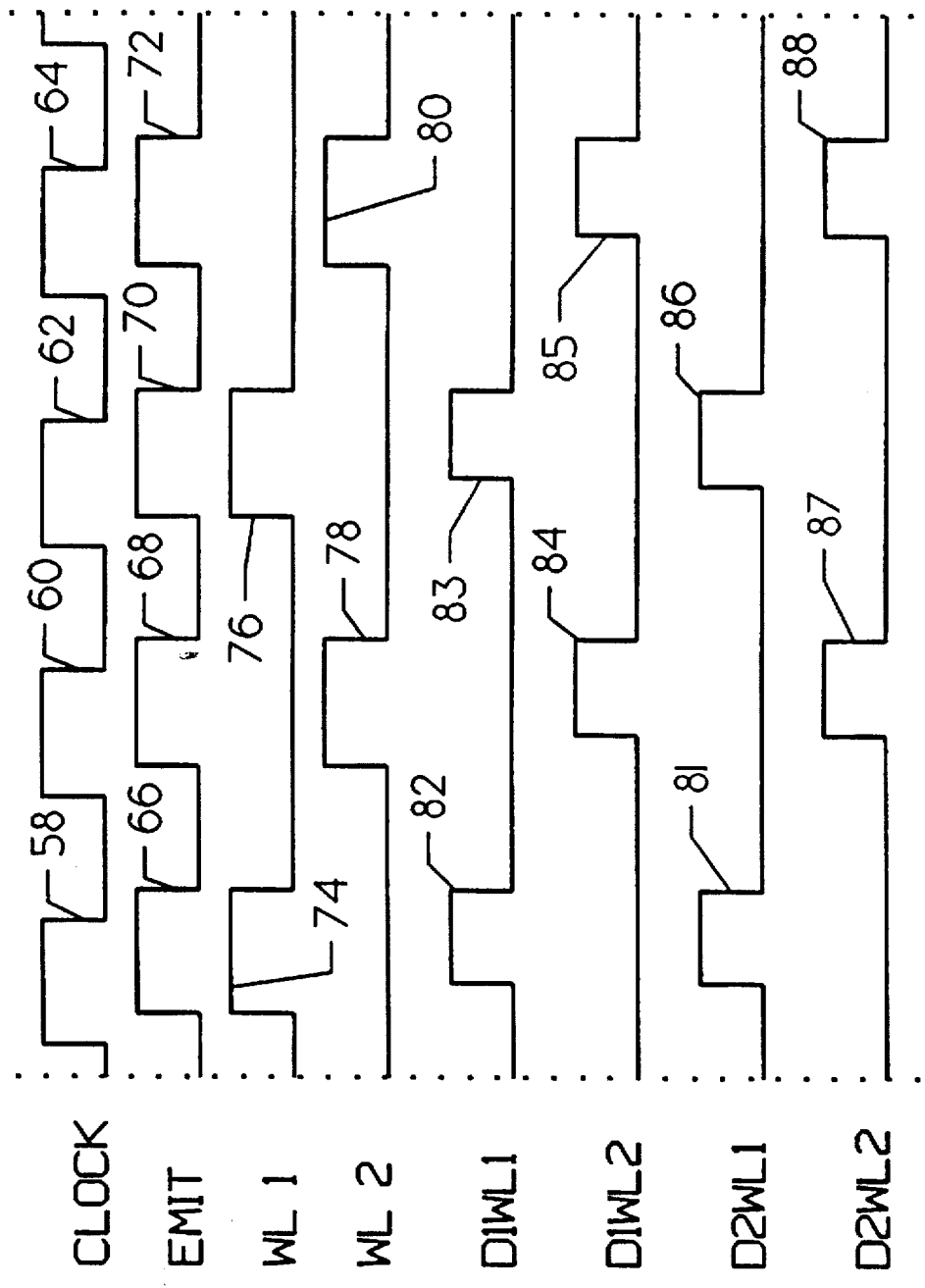
FIG. 5 is a timing diagram for the operation of the embodiment of FIG. 4.

FIG. 5 is a timing diagram for the apparatus of FIG. 4. The clock signal, containing pulses 58, 60, 62, and 64, is produced by Pattern Generator 44 (see also FIG. 4). The clock pulses are preferably produced at a rate of about 1600 hz. Each of the clock pulses triggers an output of emitter 16 as shown by pulses 66, 68, 70, and 72. The first wavelength is emitted twice corresponding to timing signals 74 and 76. Thereafter, the second wavelength is emitted twice corresponding to timing signals 78 and 80.

The signal from the first wavelength as received by detector 20 is gated to Analog/Digital converter 46 by DMUX 42 via line 50 during times 82 and 83. The signal produced by the first wavelength as received by detector 24 is gated over line 54 at times 81 and 86. Similarly, the signal from the second wavelength emission is gated over lines 52 and 54 from detectors 20 and 24 at times 84 and 85, and times 87 and 88, respectively. The received signals are converted to digital form and transferred to CPU 48 for calculation of the oxygen saturation level.

Figure 6:
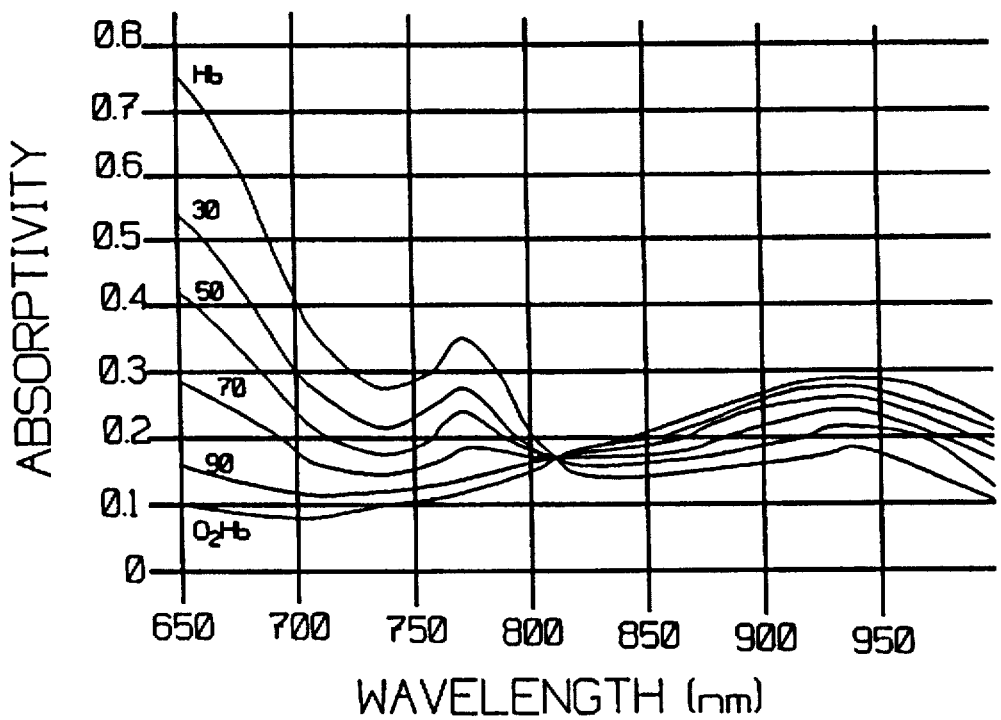
FIG. 6 is a graph of absorptivity vs. wavelength for various different oxygen saturation levels within the range of operation of the present invention.

FIG. 6 is a graphical representation of the absorptivities of the various saturation levels of arterial blood as a function of wavelength of emitter 16. The wavelengths preferred in the instant invention are about 660 nm and about 905 nm. However, those of skill in the art will readily appreciate that the present invention may be satisfactorily practiced using other wavelengths.

Figure 7:
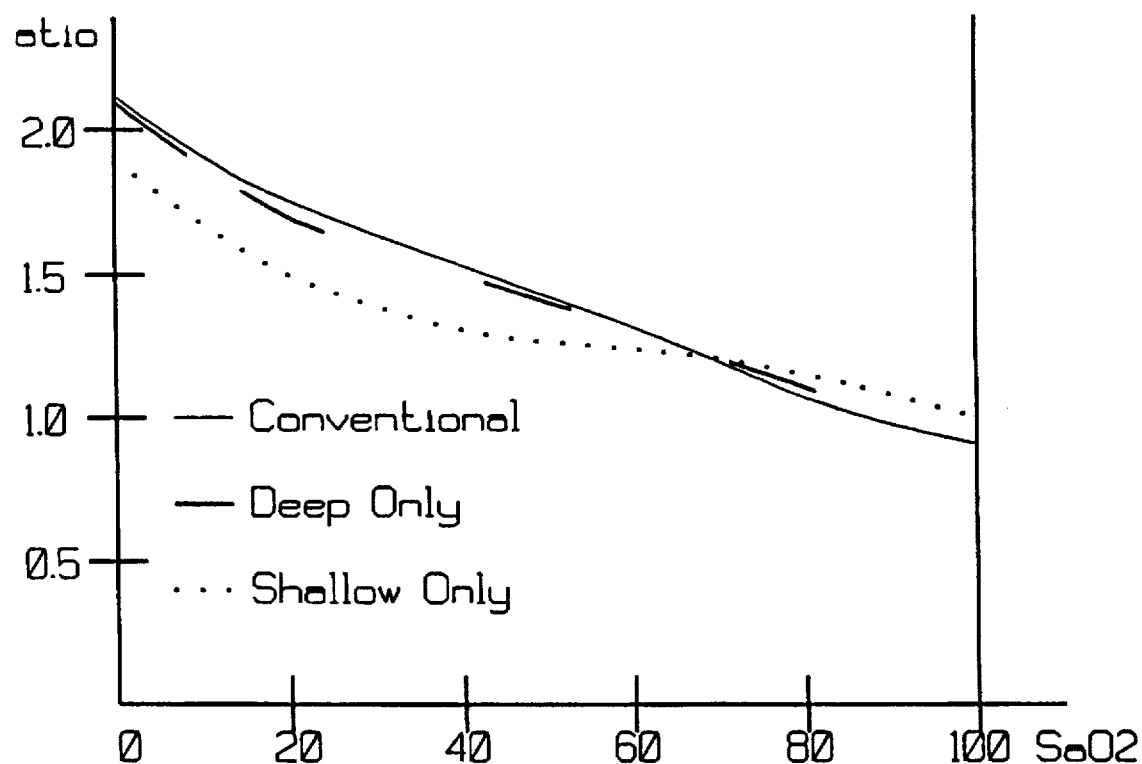
FIG. 7 is a graph comprising calculated oxygen saturation values using the principles of the invention for deep and shallow tissue measurements, and values obtained without using the principles of the invention.

FIG. 7 is a graph illustrating data obtained from computer models of arterial oxygen saturation calculated using traditional techniques for a single detector, and using first and second detectors as described in FIG. 1. As can be seen, the ratios of the Deep track very closely with the ratios from the conventional system.

Though the invention has been primarily described by reference to an apparatus having a single emitter area 16 which emits light of at least two differing and known wavelengths, and first and second separated detector areas 20, 24, it will be appreciated that the three sensor areas could also be achieved by having a single detector area and first and second separated emitter areas, each of which emit light at first and second differing and known wavelengths, as illustrated in FIG. 1B. According to a preferred embodiment, the signals are transmitted by the emitters and detected by the detectors using standard time signal multiplex techniques, though other signal multiplex techniques could alternately be used if desired (e.g. frequency multiplex). In addition, increased resolution between differing tissue layers is achievable if increased number of sensor areas is utilized. For example, a half dozen or more detector areas could be utilized in combination with a single emitter area, or half dozen or more dual wavelength emitter areas could be utilized in combination with a single detector area. In addition, the sensor areas could be aligned in a linear array, either straight or curved, or could be disposed in a two-dimensional array. Each different emitter/detector spacing pair could be used to calculate an oxygen saturation using different pulse oximetry signal processing methodologies as disclosed, and these multiple saturation values could be processed to image the tissue layers beneath the sensor areas or to reveal other desired information regarding these tissue layers.

Having thus described the preferred modes of the present invention, those of ordinary skill in the art will be readily able to think of yet other embodiments within the scope of the claims hereto attached and wherein:

I claim:

1. An apparatus comprising:
   a. a patient interface adapted to be coupled to a patient;
   b. an emitter of electromagnetic radiation coupled to said patient interface;
   c. a first detector coupled to said patient interface at a first distance from said emitter;
   d. a second detector coupled to said patient interface at a second distance from said emitter;
   e. means for synchronizing an oxygen saturation measurement to a predetermined portion of a cardiac cycle of said patient; and
   f. means coupled to said first and said second detectors and said synchronizer for computing an oxygen saturation level of arterial blood of said patient, at a predetermined tissue level of interest, with an algorithm that filters out pulsatile signal contributions from a second predetermined tissue level.

2. An apparatus according to claim 1 wherein said emitter emits a plurality of predetermined wavelengths of electromagnetic radiation.

3. An apparatus according to claim 2 wherein said emitter emits two predetermined wavelengths of electromagnetic radiation.

4. A pulse oximeter apparatus for calculating arterial oxygen saturation, comprising:
   a. a patient interface adapted to be coupled to a patient and including at least three sensor areas for emitting electromagnetic radiation which penetrates tissue of the patient and detects that electromagnetic radiation scattered by the tissue, a first spacing being between a first combination of electromagnetic emitter which emits at least two wavelengths and electromagnetic detector a second spacing being between a second combination of electromagnetic emitter which emits at least two wavelengths and electromagnetic detector, the first spacing being different from the second spacing; and
   b. means for calculating an arterial oxygen saturation level of the patient in response to the detected electromagnetic radiation, at a predetermined tissue level of interest, with an algorithm that filters out pulsatile signal contributions from a second predetermined tissue level.

5. A method of measuring oxygen saturation level of arterial blood at a measurement site of a patient comprising:
   a. determining a time of arrival of an arterial pulse wavefront at the measurement site of the patient;
   b. emitting a first wavelength of electromagnetic radiation at the measurement site of the patient;
   c. measuring an amplitude of the first wavelength of electromagnetic radiation at a first detector located at a first distance from the measurement site;
   d. measuring an amplitude of the first wavelength of electromagnetic radiation at a second detector located at a second distance from the measurement site;
   e. emitting a second wavelength of electromagnetic radiation at the measurement site of the patient;
   f. measuring an amplitude of the second wavelength of electromagnetic radiation at the first detector located at the first distance from the measurement site;
   g. measuring an amplitude of the second wavelength of electromagnetic radiation at the second detector located at the second distance from the measurement site;
   h. computing an arterial oxygen saturation level, at a predetermined tissue level of interest, with an algorithm that filters out pulsatile signal contributions from a second predetermined tissue level, using the amplitudes of the first wavelength measured at the first detector and the second detector, using the amplitudes of the second wavelength measured at the first detector and the second detector, and rejecting oxygen saturation level of venous blood of the patient.

6. A method of measuring a blood characteristic at a measurement site of a patient comprising:
   a. determining a time of arrival of an arterial pulse wavefront at the measuring site of the patient;
   b. emitting a first wavelength of electromagnetic radiation at the measurement site of the patient;
   c. measuring an intensity of the first wavelength of electromagnetic radiation at a first detector located at a first distance from the measurement site;
   d. measuring an intensity of the first wavelength of electromagnetic radiation at a second detector located at a second distance from the measurement site;
   e. emitting a second wavelength of electromagnetic radiation at the measurement site of the patient;
   f. measuring an intensity of the second wavelength of electromagnetic radiation at the first detector located at the first distance from the measurement site;
   g. measuring an intensity of the second wavelength of electromagnetic radiation at the second detector located at the second distance from the measurement site;
   h. determining a blood characteristic level, at a predetermined tissue level of interest, with an algorithm that filters out pulsatile signal contributions from a second predetermined tissue level, using the intensities of the first wavelength measured at the first detector and the second detector, using the intensities of the second wavelength measured at the first detector and the second detector, and rejecting blood characteristic level of venous blood of the patient.

* * * * *